(12) United States Patent
Horrobin

(10) Patent No.: US 6,479,544 B1
(45) Date of Patent: Nov. 12, 2002

(54) THERAPEUTIC COMBINATIONS OF FATTY ACIDS

(75) Inventor: David Frederick Horrobin, Stirling (GB)

(73) Assignee: Laxdale Limited, Stirling (GB)

( * ) Notice: Subject to any disclaimer, the term of this patent is extended or adjusted under 35 U.S.C. 154(b) by 0 days.

(21) Appl. No.: 09/893,473

(22) Filed: Jun. 29, 2001

(30) Foreign Application Priority Data

Jun. 29, 2001 (GB) .............................................. 0016045

(51) Int. Cl.$^7$ .............................................. A61K 31/23
(52) U.S. Cl. ........................................ 514/552; 514/558
(58) Field of Search ................................. 514/558, 552

(56) References Cited

U.S. PATENT DOCUMENTS

| | | | |
|---|---|---|---|
| 4,526,902 A | 7/1985 | Rubin | 514/560 |
| 4,977,187 A | 12/1990 | Horrobin | 514/560 |
| 5,120,760 A * | 6/1992 | Horrobin | 514/458 |
| 5,198,468 A * | 3/1993 | Horrobin | 514/558 |
| 5,223,285 A | 6/1993 | DeMichele et al. | 426/72 |
| 5,252,333 A | 10/1993 | Horrobin | 424/422 |
| 5,260,067 A | 11/1993 | Zheng | 424/450 |
| 5,378,732 A | 1/1995 | Horrobin et al. | 514/560 |
| 5,466,841 A * | 11/1995 | Horrobin et al. | 554/79 |
| 5,516,800 A | 5/1996 | Horrobin | 514/560 |
| 5,516,801 A | 5/1996 | Horrobin et al. | 514/560 |
| 5,562,913 A * | 10/1996 | Horrobin | 424/401 |
| 5,658,767 A * | 8/1997 | Kyle | 435/434 |
| 5,993,221 A * | 11/1999 | Bistrian | 435/429 |
| 5,998,476 A * | 12/1999 | Sleigh et al. | 514/560 |
| 6,184,251 B1 * | 2/2001 | Stordy et al. | 514/560 |
| 6,274,747 B1 * | 8/2001 | Strelchenok | 554/40 |

FOREIGN PATENT DOCUMENTS

| | | |
|---|---|---|
| EP | 0609078 A1 | 8/1994 |
| EP | 0 711 503 | 5/1996 |
| EP | 0 713 653 | 5/1996 |
| WO | 99/33355 | 7/1999 |
| WO | WO00/21524 | 4/2000 |
| WO | WO00/44361 | 8/2000 |

OTHER PUBLICATIONS

Ann Nutr Metab, Meeting Report No. 43, Simopoulos et al, "Essentiality of and Recommended . . . "pp. 127–130, 1999.
ISSFAL Newsletter reporting on the International Society for the Study of Fatty Acids and Lipids, pp. 1–5, 1999 workshop.
WPI Japanese Abstract No. 1989–290735 (JP 010215245), 1989.
XP–002181361; Song; Sep. 27, 1994; Derwent Publications Ltd., London, GB; Section Ch, Week 199932.
XP–002181362; Tokiwa Yakuhin Kogyo KK; Sep. 27, 1994; Derwent Publications Ltd., London, GB; Section Ch, Week 199443.
XP–002181364; Tokiwa Yakuhin Kogyo KK; Jun. 29, 1993; Derwent Publications Ltd., London, GB, Section Ch, Week 199330.
XP–002181363; Nissei Marine Kogyo KK; Jun. 17, 1992; Derwent Publications Ltd., London, GB; Section Ch, Week 199231.
Patent Abstracts of Japan; 60 132916; Jul. 16, 1985; vol. 009; No. 187 (C–314); Fujita Tadashi.

\* cited by examiner

*Primary Examiner*—James H. Reamer
(74) *Attorney, Agent, or Firm*—Jacobson Holman PLLC

(57) ABSTRACT

Eicosapentaenoic acid or any appropriate derivative (EPA) is disclosed in combination with arachidonic acid (AA) or an AA precursor, selected from DGLA and GLA, to give a pharmaceutical formulation.

15 Claims, 1 Drawing Sheet

THERAPEUTIC COMBINATIONS OF FATTY ACIDS

There are two series of essential fatty acids (EFAs) in humans. They are termed "essential" because they cannot be synthesised de novo in mammals. Their metabolic pathways are shown in FIG. 1. These fatty acids can be interconverted within a series, but the omega-6 (n-6) series cannot be converted to the omega-3 series nor can the omega-3 (n-3) series be converted to the omega-6 series in humans. The main EFAs in the diet are linoleic acid of the omega-6 series and alpha-linolenic acid of the omega-3 series. However, to fulfil most of their biological effects these "parent" EFAs must be metabolised to the other fatty acids shown in FIG. 1. Each fatty acid probably has a specific role in the body. Particularly important in the n-6 series are dihomogamma-linolenic acid (DGLA, 20:3n-6) and arachidonic acid (AA, 20:4n-6), while particularly important in the n-3 series are eicosapentaenoic acid (EPA, 20:5n-3) and docosahexaenoic acid (22:6n-3). This patent specification particularly concerns combinations of AA and EPA.

AA is found as an important constituent of all cell membranes and particularly of cell membranes of nerve cells. It is an important component of many signal transduction systems which are activated by many different forms of cell stimulation. AA is usually found in cells in the form of phospholipids. Cell activation generates a range of active phospholipases which can release AA as the free acid. The free acid has many direct actions of its own in regulating protein kinases and other enzymes, in modulating movements of calcium and other ions, in activating receptors such as peroxisome proliferator activated receptors (PPARs), and in modulating gene function. Furthermore AA can be converted to an enormous range of even more active derivatives known by the general name of eicosanoids. These include prostaglandins, leukotrienes, thromboxanes, various types of hydroxy acids, lipoxins, hepoxilins and many other compounds. These substances are often involved in inflammatory and thrombotic reactions and are frequently regarded as harmful in their overall effects. This harmful image is illustrated by the fact that intravenous AA is frequently lethal because of its thrombotic effects, and by the fact that the steroids which are widely used, in particular for their anti-inflammatory effects, block the release of AA by phospholipases. Moreover, the class of drugs known as cyclo-oxygenase inhibitors, which include aspirin and many other well known compounds, known for their antithrombotic and anti-inflammatory effects, inhibit the conversion of AA to prostaglandins and thromboxanes.

This concept of the potential toxicity of AA has become well established. The expert organisation in the field, the International Society for the Study of Fatty Acids and Lipids (ISSFAL) in 1999 organised a workshop in association with the US National Institutes of Health. The remit of the workshop was to make recommendations concerning the human uses of EFAs. The participants, all leading experts in the field, had no doubts about the harmful effects of AA, and emphasised this in their final statement (AP Simopoulos et al, Essentiality of and recommended dietary intakes for omega-6 and omega-3 fatty acids, Nutrition and Metabolism 1999; 43:127–130). The ISSFAL newsletter reporting on this workshop stated that "after much discussion, consensus was reached on the importance of reducing the omega-6 polyunsaturated fatty acids (PUFAs) even as the omega-3 PUFAs are increased in the diet of adults and newborns for optimal brain and cardiovascular function. This is necessary to reduce adverse effects of arachidonic acid and its eicosanoid products".

In contrast to this general view of AA toxicity, the experts of ISSFAL and NIH were keen to promote the value of the n-3 EFAs, particularly EPA and DHA for human health. The view was taken that EPA and DHA would replace AA in cell membrane phospholipids and also reduce AA synthesis from linoleic acid. The lowering of AA levels by EPA and/or DHA was expected to have widespread beneficial effects on human health.

The present invention results from recent surprising observations of the inventor which suggest that this view may be wrong. Contrary to the general expert opinion, it has now been found that AA is highly desirable rather than undesirable and it may be helpful to administer AA in association with EPA. The present invention provides this combination treatment.

The present invention provides pharmaceutical formulations containing eicosapentaenoic acid or any appropriate derivative (hereinafter collectively referred to as EPA) and arachidonic acid (AA), as set out in the claims attached hereto. AA may be replaced by one or more of its precursors, DGLA or GLA. The ratio of EPA to AA is preferably between 1:1 and 20:1.

The EPA is preferably provided in a dose of between 100 mg and 10,000 mg/day. The formulation may be a single preparation comprising 100–10,000 mg EPA. An alternative upper limit is 5,000 mg EPA. Preferably, the formulations of the invention comprise 1–4 g EPA and 0.1–2.0 g arachidonic acid (AA). Still preferred amounts are 1.5–3 g EPA and 0.2–1 g AA.

The formulation may be a single daily dose preparation to give in one dose the above intakes, or may be in convenient divided doses, for example, a daily dose formed of four soft gelatin or other capsules, each containing 500 mg of EPA in an appropriate form and 150 mg of AA in an appropriate form.

The compositions of the first aspect of the present invention are prepared by combining EPA in biologically assimilable form in which the EPA is at least 50% pure, preferably at least 90% pure, and arachidonic acid (AA) in any biologically assimilable form. The starting materials must include one containing substantial amounts of the EPA. The same can apply for the AA, which may be at least 30% pure, preferably at least 90% pure.

Still preferably, the active ingredient of the formulations of the present invention consists essentially wholly of the EPA and AA or AA precursor. In that case, no significant amounts of other EFAs are present.

Flavourants or emulsifiers may be included to make the preparation palatable. Other conventional additives, diluents and excipients may be present. The preparation for ingestion may be in the form of a capsule, a dry powder, a tablet, an oil, an emulsion or any other appropriate form. The capsules may be hard or soft gelatin capsules, agar capsules, or any other appropriate capsule.

The EPA is preferably composed of a triglyceride or ethyl ester which is 50% pure or purer, more preferably more than 90% pure. Other forms of the fatty acids which may be useful include the free acids, salts, esters of any type, amides, mono-, di- or triglycerides, phospholipids or any other form which can lead to the incorporation of EPA into body tissues. If phospholipids are considered, it is specifically excluded from the present invention that a phospholipid containing two different fatty acids, that is containing both EPA and AA (or AA precursor) is used. Phospholipids containing EPA may however be used in the present formulations when combined with phospholipids containing AA or AA precursor.

The formulations of the present invention may be used for the treatment of a wide range of diseases and disorders including:

any psychiatric, neurological or other central or peripheral nervous system disease—in particular schizophrenia, depression, bipolar disorder and degenerative disorders of the brain including Alzheimer's disease and other dementias and Parkinson's disease;

asthma and other respiratory diseases;

diseases of the gastrointestinal tract including inflammatory bowel diseases and irritable bowel syndrome;

inflammatory disease affecting any system;

cardiovascular disease;

dyslipidaemia, any form of diabetes or any form of metabolic diseases;

dermatological diseases;

kidney or urinary tract diseases;

liver diseases;

disease of the male or female reproductive organs such as the breast or the prostate gland;

cancer or cancer cachexia;

diseases of the head and neck, including disease of the mouth and teeth, of the eyes or of the ears;

infection with viruses, bacteria, fungi, protozoa or other organisms.

They may also be taken as a general nutritional supplement.

The present invention further provides a method of treatment or prevention of any of the aforesaid diseases or conditions, in particular neurological and psychiatric disorders, especially schizophrenia, depression, bipolar disorder and degenerative disorders of the brain including Alzheimer's disease and other dementias and Parkinson's disease. The treatment or preventative method is, for example, by the combined application of EPA and AA at the dosage regime of between 100 mg and 10,000 mg/day EPA and a ratio of EPA to AA of between 1:1 and 20:1. A precursor to AA, selected from DGLA and GLA, may be used instead of AA. The preferred range of EPA to AA (or its precursor) is between 1:1 and 5:1.

The present invention still further provides a method of treatment or prevention of any disease selected from:

asthma and other respiratory diseases;

diseases of the gastrointestinal tract including inflammatory bowel diseases and irritable bowel syndrome;

inflammatory disease affecting any system;

cardiovascular disease;

any form of dyslipidaemia, any form of diabetes or any form of metabolic diseases;

any form of dermatological diseases;

any form of kidney or urinary tract disease;

any form of liver disease;

any form of disease of the male or female reproductive system or related secondary sexual organs such as the breast or prostate gland; any form of cancer or for cancer cachexia;

any disease of the head and neck including diseases of the mouth and teeth, of the eyes or of the ears; and any form of infection with viruses, bacteria, fungi, protozoa or other organisms by, for example, the combined application of EPA and AA at the dosage regime of between 100 mg and 10,000 mg/day EPA and a ratio of EPA to AA of between 1:1 and 20:1. A precursor to AA, DGLA or GLA, may be used instead of AA. The preferred range of EPA to AA (or its precursor) is between 1:1 and 5:1.

Use of the formulations of the invention in the manufacture of a medicament for the treatment or prevention of any disease or disorder, including those mentioned above, is included in the present invention.

The specific therapeutic compositions proposed are ones which provide not less than 100 mg and not more than 10,000 mg of EPA/day combined with AA, DGLA or GLA, in doses of between 100 mg and 10,000 mg/day. An alternative upper limit is 5,000 mg/day of the fatty acids. Particularly preferred amounts are 1–4 g per day EPA combined with 0.1–2.0 g per day arachidonic acid, or one of its precursors, GLA or DGLA. A still preferred composition comprises 1.5–3 g EPA and 0.2–1 g AA. The present invention further provides a formulation, for example, in a one-a-day dose comprising 1.5–3 g EPA and 0.1–2.0 g arachidonic acid or one of its precursors.

The ratio of EPA to the omega-6 fatty acid is important because too much EPA is likely to lead to the loss of AA from membranes, while too much AA may lead to adverse effects because of excessive conversion of AA to eicosanoid. The ratio of EPA to AA or DGLA or GLA should therefore never be less than 1:1, should preferably be in the range between 20:1 and 1:1, and should still preferably be in the range of between 5:1 and 1:1. These combinations will ensure that the beneficial effects of EPA are enhanced and maintained even at relatively high EPA doses, because the provision of AA and its precursors will prevent AA depletion which may occur when too much EPA is given alone.

During absorption from the gut and within the body, EPA moieties are readily transformed intact from one chemical form to another. Simple esters such as ethyl or methyl esters are readily split by esterases and the freed fatty acids can then be bound by albumin or other binding or transport proteins or incorporated into complex lipids such as phospholipids, cholesterol ester or glycerides. The fatty acids in the present formulations can therefore be administered in any form such as glycerides, esters, free acids, salts, phospholipids, amides or any other form which leads to their incorporation into the blood and cell membranes.

The EPA, AA, DGLA or GLA may be derived from any appropriate source including plant seed oils, microbial oils from algae or fungal or marine oils from fish or other marine animals. They may be used in the form of the natural oil, if that oil meets the required purity requirements of the starting material, or may be purified to give products containing 30%, 40%, 50%, 60%, 70%, 80%, 90% or more of the fatty acid. A particularly useful form of EPA is the highly purified ethyl ester described in patent filings based on the preliminary UK filing 9901809.5. Synthetic routes to the fatty acids are also possible although at present are not economically feasible.

Once the oils containing the individual fatty acids have been obtained, and purified as necessary, the starting materials may be blended to give the desirable ratios of EPA to AA, DGLA or GLA described above.

The blended fatty acid compositions may then be incorporated into any appropriate dosage form for oral, enteral, parenteral, rectal, vaginal, dermal or other route of administration. Soft or hard gelatin capsules, flavoured oil blends, emulsifiers or other liquid forms, and microencapsulate powders or other dry form vehicles are all appropriate ways of administering the products.

Example Formulations (a) Soft or hard gelatin capsules each containing 500 mg or 1000 mg of a mix of 10 parts 95% pure ethyl-EPA to 2 parts of 95% pure AA;

(b) As in (a) but where the AA and EPA ethyl esters are replaced with the fatty acids in any other appropriate bioassimilable form such as the free acid, tri-, di- or monoglyceride, other esters, salts such as the sodium, potassium or lithium salts, amides, phospholipids or any other appropriate derivatives;

(c) As in (a) or (b) but where the EPA or EPA derivative is 50%, 60%, 70%, 80% or 90% pure and where the AA or AA derivative is 30%, 40%, 50%, 60%, 70%, 80% or 90% pure;

(d) As in (a)–(c) but where the ratio of EPA to AA is anywhere in the range from 1:1 to 20:1;

(e) As in (a)–(d) but where the material is in the form of a microencapsulated powder which can be used as a powder or compressed into tablets. Such powders may be prepared by a variety of technologies known to those skilled in the art;

(f) As in (a)–(d) but where the formulation is a liquid or emulsion, appropriately flavoured for palatable oral administration;

(g) As in (a)–(d) but where the material is formulated in to material appropriate for topical application such as a cream or ointment;

(h) As in (a)–(g) but where the AA is replaced by one of its precursors, GLA or DGLA.

EXPERIMENTAL DATA

Figure 1:
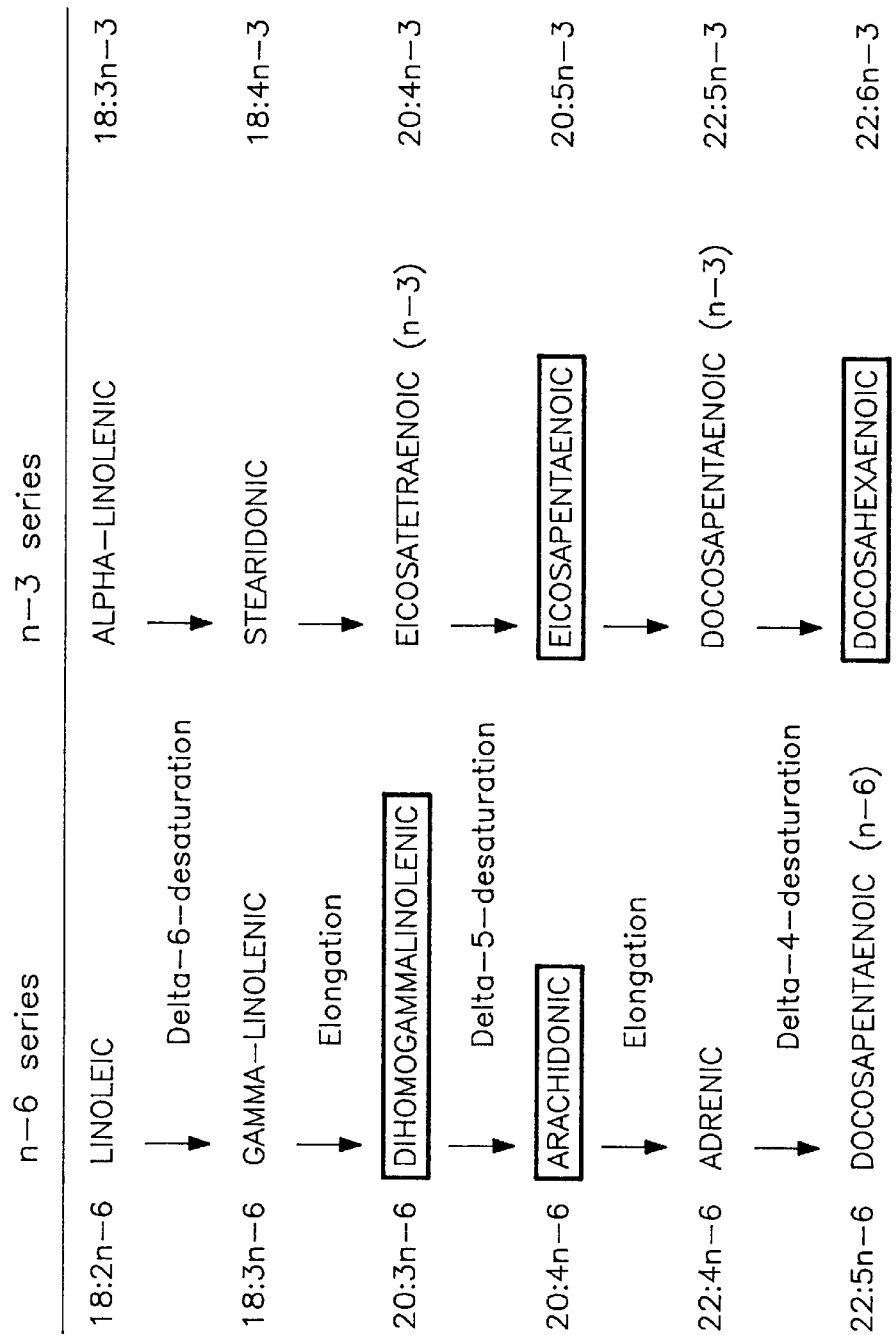
FIG. 1. the metabolic pathways of the two series of essential fatty acids.

A trial was conducted of the administration of a placebo and three different doses of EPA, 1 g, 2 g and 4 g/day in the treatment of schizophrenia in patients who were also taking the antischizophrenic drug clozapine. Previous pilot studies had suggested that EPA would have desirable effects and the expectation was that the higher the dose of EPA, the better would be the effect. 31 patents were entered into the study and followed for 12 weeks. They were assessed at baseline and 12 weeks using the Positive and Negative Symptom Scale for Schizophrenia (PANSS). The percentage improvements from baseline are shown in table 1. Placebo produced a small effect, 1 g/day produced a larger effect, 2 g/day produced a large effect of 26.0% compared to the usual 15–20% improvements on this scale generated by existing drugs for schizophrenia. It was expected that 4 g/day would produce the best effect but this did not happen. The effect of 4 g/day while there, was substantially less than the effect of 2 g/day, and comparable to that of 1 g/day.

TABLE 1

Percentage improvements from baseline to 12 weeks on the Positive and Negative Symptom Scale for Schizophrenia (PANSS) in patients given placebo, 1 g/day, 2 g/day or 4 g/day ethyl eicosapentaenoate

|  | Placebo | 1 g | 2 g | 4 g |
|---|---|---|---|---|
| n | 7 | 9 | 9 | 6 |
| Improvement | 6.0% | 18.3% | 26.0% | 16.3% |

In these patients, and also in a further series of patients, the levels of DGLA, AA, EPA and DHA were measured in human red cells before starting treatment and after 12 weeks. The results were partly expected and partly surprising and are shown in table 2. As expected there was a dose-related rise in EPA which was greater the greater the dose. It was also expected that there would be a progressive decline in AA, the larger the EPA dose, the greater the fall in AA. However, this did not happen. 1 g/day of EPA produced a small rise in AA while 2 g/day produced a large rise. 4 g/day EPA produced the expected fall in AA.

TABLE 2

Changes from baseline to 12 weeks in red cell concentrations (in µg/g) of eicosapentaenoic acid (EPA) and arachidonic acid (AA) in red blood cells in tour groups of schizophrenic patients given placebo or 1 g/d, 2 g/d or 4 g/d ethyl-EPA. + means a rise and − means a fall

|  | Placebo | 1 g | 2 g | 4 g |
|---|---|---|---|---|
| EPA | −0.6 | +2.4 | +33.7 | +49.0 |
| AA | −12.6 | +2.7 | +29.4 | −26.5 |

It appeared that the improvement in schizophrenic symptoms was more related to the changes in AA than to the changes in EPA. This was tested in a larger series of patients where the improvement in PANSS was correlated with the changes in all the major EFAs. The values for r, the correlation coefficient, are shown in table 3 as is the statistical significance of the relationship. An r value of 1.0 means that the two parameters are perfectly related while one of 0.0 means that there is no relationship whatsoever.

TABLE 3

Correlations between the change from baseline to 12 weeks on the total PANSS score and the change from baseline to 12 weeks in the red cell concentration of various essential fatty acids. r, the correlation coefficient from a linear regression analysis, is shown. p is the statistical significance of the relationship.

| Fatty acid | Correlation coefficient r | Significance p= |
|---|---|---|
| Dihomogammalinolenic (DGLA) | −0.51 | 0.09 |
| Arachidonic (AA) | −0.81 | 0.001 |
| Eicosapentaenoic (EPA) | −0.07 | 0.84 |
| Docosapentaenoic (DPA) | −0.12 | 0.76 |
| Docosahexaenoic (DHA) | −0.35 | 0.13 |

From the table it is clear that by far the strongest relationship is with AA, and the second strongest relationship is with DGLA. Rises in these two fatty acids are strongly associated with improvement in schizophrenic symptoms, as indicated by a fall in the PANSS score, hence the negative correlations. In contrast there is almost no relationship with EPA because high doses of EPA are associated with falls in red cell AA levels and the loss of clinical effect.

These results were completely unexpected. Far from EPA itself being the most desirable fatty acid in cell membranes it seems that AA and DGLA are more helpful. The likeliest interpretation of this is that AA is desirable when it is retained in membrane phospholipids and not converted to potentially dangerous eicosanoids. The effect of EPA may be to inhibit phospholipases and so keep AA in the phospholipid form. Very high does of EPA, however, displace AA and the therapeutic effect is lost.

This interpretation was supported by a pilot study in which AA itself was given to five patients with schizophrenia. The expectation was that they would improve, but in fact their condition deteriorated. The administration of AA, without EPA to inhibit phospholipases, may lead to increased formation of eicosanoids rather than to incorporation of AA into phospholipids.

The conclusion to be drawn from these studies is that EPA is desirable, not in itself but because it raises the AA level in membrane phospholipids. High doses of EPA, far from being valuable in themselves, may be undesirable because they lead to excessive loss of AA from membranes. The way to get around this issue, and to boost the clearly desirable effects of EPA, is to keep to relatively low doses of EPA, but also to boost the level of AA by administering the EPA with either AA or one of its precursors, DGLA or gamma-linolenic acid GLA. When AA in a dose of 1 g/day was given to two patients who had already been taking 2 g/day EPA for 3 months, they experienced a substantial further improvement without any of the worsening seen when AA was given alone.

U.S. Pat. No. 4,977,187 provided for combinations of n-3 fatty acids and n-6 fatty acids and vitamin E in the treatment of schizophrenia. However, that patent did not direct attention to AA specifically or to EPA specifically, or to the specific combination of EPA with AA or its immediate precursors or to the specific doses and ratios of EPA and AA described in this specification. Any n-6 fatty acid could be combined with any n-3 fatty acid in any ratio in U.S. Pat. No. 4,977,198 and corresponding patents.

A review of the literature suggests that the phenomenon described here is not only true of schizophrenia but of several disorders where EPA is therapeutically useful. There are many studies describing the value of low doses of EPA containing products in cardiovascular diseases, in inflammatory disease and in other disorders. However, when investigators have gone to higher doses, these desirable therapeutic effects have been lost. To take two examples, high doses of EPA completely failed to exert beneficial effects in patients undergoing angioplasty for coronary vascular disease, or in patients with inflammatory bowel disease, even though earlier studies with smaller EPA doses had given strong evidence of benefit. The authors had no real explanation for the trial failure and did not consider the possibility that excess depletion of AA may have been the cause.

The use of the formulations of the present invention could be very wide-ranging.

What is claimed is:

1. A pharmaceutical composition comprising a combination of a) a biologically assimilable eicosapentaenoic compound (EPA) having a purity of at least 90% with b) a biologically assimilable arachidonic compound (AA) or a precursor thereof having a purity of at least 90%.

2. A pharmaceutical composition according to claim 1 in which the ratio of EPA to AA or a precursor thereof is between 1:1 and 20:1.

3. A pharmaceutical composition according to claim 1 in which the EPA is provided in a dose of between 100 mg and 10,000 mg/day.

4. A pharmaceutical composition according to claim 1 comprising from 1 to 4 g EPA and from 0.1 to 2.0 g arachidonic acid.

5. A pharmaceutical composition according to claim 1 comprising from 1.5 to 3 g of EPA and from 0.1 to 2.0 g of AA or a precursor thereof.

6. A pharmaceutical composition according to claim 1 which consists essentially of a combination of (a) and (b).

7. A pharmaceutical composition according to claim 1 wherein the AA precursor is in the form of DGLA.

8. A pharmaceutical composition according to claim 1 wherein the AA precursor is in the form of GLA.

9. A pharmaceutical composition according to claim 1 wherein the AA precursor is a member selected from the group consisting of DGLA and GLA, and the EPA is provided in a dose of between 100 mg and 10,000 mg/day, and the ratio of EPA to AA precursor is between 1:1 and 20:1.

10. A pharmaceutical composition according to claim 1 further comprising a flavourant or emulsifier.

11. A pharmaceutical composition according to claim 1 wherein the EPA is in triglyceride or ethyl ester form.

12. A method of treating or preventing a psychiatric, neurological or other central or peripheral nervous system disease which comprises administering to a subject prone to or afflicted with such disease an effective amount of a composition according to claim 1.

13. A method according to claim 12 wherein the disease is schizophrenia, depression, bipolar disorder, Alzheimer's disease, other dementia or Parkinson's disease.

14. A method of treating or preventing a disease which comprises administering an effective amount of a composition according to claim 1 to a subject prone to or afflicted with such disease, and wherein the disease is an amenable disease selected from the group consisting of:

asthma or other respiratory disease;
   a disease of the gastrointestinal tract;
   an inflammatory disease;
   a cardiovascular disease;
   a dyslipidaemia, diabetes or other form of metabolic disease;
   a dermatological disease;
   a kidney or urinary tract disease;
   a liver disease;
   a disease of the male or female reproductive system or related secondary sexual organs;
   a cancer;
   a disease of the head or neck; and
   an infection caused by a virus, bacterium, fungus, protozoa or other organism.

15. A pharmaceutical composition according to claim 1 wherein its sole active ingredient consists essentially of the combination of (a) with (b).

* * * * *